(12) United States Patent
Ginsberg

(10) Patent No.: US 8,011,625 B2
(45) Date of Patent: Sep. 6, 2011

(54) SUPPORT FOR MEDICAL EQUIPMENT

(75) Inventor: Steven H. Ginsberg, Bridgewater, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 12/613,954

(22) Filed: Nov. 6, 2009

(65) Prior Publication Data
US 2010/0116946 A1    May 13, 2010

Related U.S. Application Data

(60) Provisional application No. 61/198,624, filed on Nov. 6, 2008.

(51) Int. Cl.
*A47F 5/08* (2006.01)
(52) U.S. Cl. .................... 248/205.1; 248/68.1
(58) Field of Classification Search ............. 5/503.1, 5/507.1, 658, 659; 248/68.1, 205.1, 65
See application file for complete search history.

(56) References Cited

U.S. PATENT DOCUMENTS

| | | | | |
|---|---|---|---|---|
| 3,298,648 | A * | 1/1967 | Sepanski | 248/103 |
| 4,465,255 | A * | 8/1984 | Hill | 248/441.1 |
| 4,998,277 | A * | 3/1991 | Rioux, Jr. | 379/454 |
| 5,054,723 | A * | 10/1991 | Arnold | 248/65 |
| 5,067,677 | A * | 11/1991 | Miceli | 248/68.1 |
| 5,094,418 | A * | 3/1992 | McBarnes et al. | 248/286.1 |
| 5,254,110 | A * | 10/1993 | Marcus et al. | 604/322 |
| 5,362,021 | A * | 11/1994 | Phillips | 248/276.1 |
| 5,433,432 | A * | 7/1995 | Adler | 473/472 |
| 5,737,783 | A * | 4/1998 | Antinori | 5/411 |
| 5,787,530 | A * | 8/1998 | Brix | 5/662 |
| 6,951,324 | B2 * | 10/2005 | Karamanos | 248/68.1 |
| 2003/0222185 | A1* | 12/2003 | Rubenstein et al. | 248/68.1 |
| 2003/0230697 | A1* | 12/2003 | Melius | 248/503 |
| 2006/0031989 | A1* | 2/2006 | Graham et al. | 5/610 |
| 2006/0169850 | A1* | 8/2006 | Wunderlich et al. | 248/68.1 |
| 2010/0108824 | A1* | 5/2010 | Patchett et al. | 248/68.1 |

* cited by examiner

*Primary Examiner* — Ramon Ramirez
(74) *Attorney, Agent, or Firm* — Licata & Tyrrell P.C.

(57) ABSTRACT

This invention relates to novel "bracket" to be used in the operating room of hospitals. The bracket of the invention holds a transducer at the level of a patient's heart in order to easily and accurately record pressures during surgery.

3 Claims, 3 Drawing Sheets

SUPPORT FOR MEDICAL EQUIPMENT

This invention relates to novel "bracket" to be used in the operating room of hospitals. The bracket of the invention holds a transducer at the level of a patient's heart in order to easily and accurately record pressures during surgery.

Transducers are commonly used in operating rooms and intensive care units. They allow tracking several values of the patients such as blood pressure, intracranial pressure, cardiac pressures. Transducers are used to convert mechanical energy into electrical energy and give the practitioner a wave form on a screen. This wave form has a numerical value attached to it. The transducer needs to be at the approximate level of the patient's right atrium.

In the operating room, transducers are typically held in place by a transducer holder which is attached to an intravenous pole. This transducer needs to maintain a constant relationship or level with the patient's body. During operations, the operating room table where the patient lies, is regularly moved. This changes the orientation. If an adjustment is made to the operating room table and the transducer is not moved similarly then the values related to the patient will be false. With the constant changes to the operating room table height during surgery this transducer would need to be moved throughout the surgery in order to give an accurate result. The practitioner needs to remember to adjust the position of the transducer throughout surgery in order to maintain the relationship in height with the atrium to obtain accurate values. Some hospitals will make their own bracket out of a metal rod which is attached to the operating room table in order to hold the transducer in its place. In these cases one will find it difficult to find a bracket holder when needed. They are not readily available at each location.

Thus there remains a need for improved brackets for use in the operating room that can maintain constant height with respect to the height of the patient on an operating table and that can have support for additional equipment used in the treatment of a patient.

SUMMARY OF THE INVENTION

In one aspect, the invention is directed to a bracket that can be placed in contact with the operating table so that when the operating room table is moved the bracket stays in contact with the table and remains at a constant height with respect to the operating table.

In another aspect, the invention further comprises support for additional equipment necessary during the course of an operating room procedure, more particularly equipment used by an anesthesiologist.

DETAILED DESCRIPTION OF THE INVENTION

The present invention provides a bracket comprising a pole, support for apparatus such as breathing circuits and a means for holding the bracket to a bed. The pole allows a transducer holder to be attached or clamped to it. The bracket can be held to the bed by slipping a portion of it between the bed and the mattress or it can be clamped to the bed.

In one embodiment of the invention a device, whose initial form is similar to a metal device presently used to hold breathing circuits for the anesthesiologist has been elegantly changed and appropriately modified to serve a dual purpose. The device that has been modified is often called a "Christmas tree". It is of metal construction and along its sides exists indentations which can act as support for the plastic tubing in a breathing circuit used during mechanical ventilation. In common examples, these are about ⅞ inch wide by about 1 ½ inches in depth. This "Christmas tree", metal stand is commonly used during operations of all types and available in each operating room.

Figure 1:
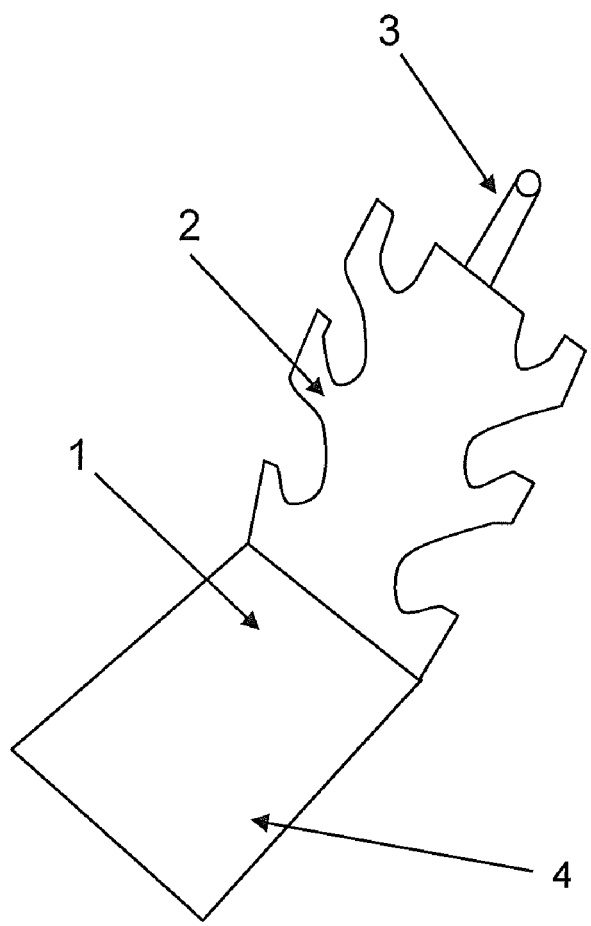
FIG. 1 is a depiction of a preferred embodiment of the invention wherein support for additional equipment is found on both sides of the pole to which a transducer holder is attached.

In a preferred embodiment of the invention, as shown in FIG. 1, the metal stand (1) is approximately 6 inches in width by 22 inches in length. The length is divided at about 9 inches by a 90 degree bend. It therefore has two sections, one of about 9 inches and one of about 13 inches. It is about ⅛ of an inch in thickness. Along the midpoint rise of its vertical (on the 13 inch side) side (2), a dowel or metal pole (3), about ⅝ inches in diameter, is mounted. In use, the bottom section (4) is positioned between a bed and the mattress.

Figure 2:
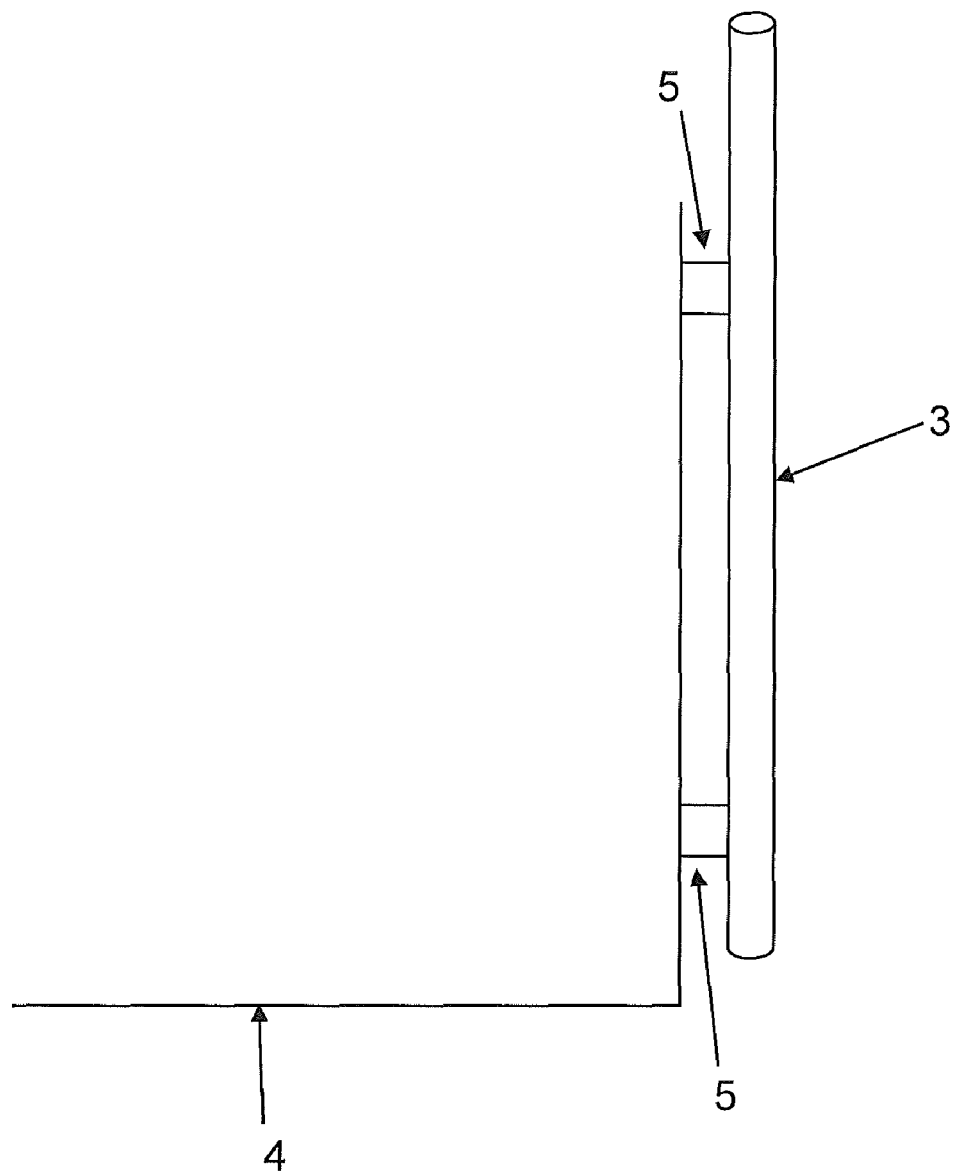
FIG. 2 is a depiction of the side view of the device shown in FIG. 1.

It is supported at the top and the bottom, as shown in FIG. 2, by a small piece of plastic or metal (5) which protrudes approximately 1 inch from the surface. The purpose is to attach and hold a transducer bracket which screws onto this dowel or pole. It thereby allows for various levels of adjustment in height so that it can constantly be kept at the level of the middle ear or right atrium as needed. One transducer holder which presently exists has an adjustment screw to attach to this dowel or pole.

The transducer is a one patient use item which gets placed into a transducer holder. Both of these items presently exist. The transducer holder which holds the transducer is what gets leveled with the atrium. By using this new device with the dowel type attachment, its horizontal bend would be placed under the mattress of the operating room table and therefore would get adjusted at the beginning of the surgery and then because of its location it would automatically move with any table adjustment; thereby maintaining the relationship between the transducer being held in place and the right atrium. This would make the transducer holder readily available in all locations and have a dual function. As such, the novel brackets described in this invention allow obtaining accurate critical readings about the patient throughout the surgical procedure without the undue need for the practitioner to remember to adjust the relationship of the transducer's height with the atrium to obtain accurate values.

Figure 3:
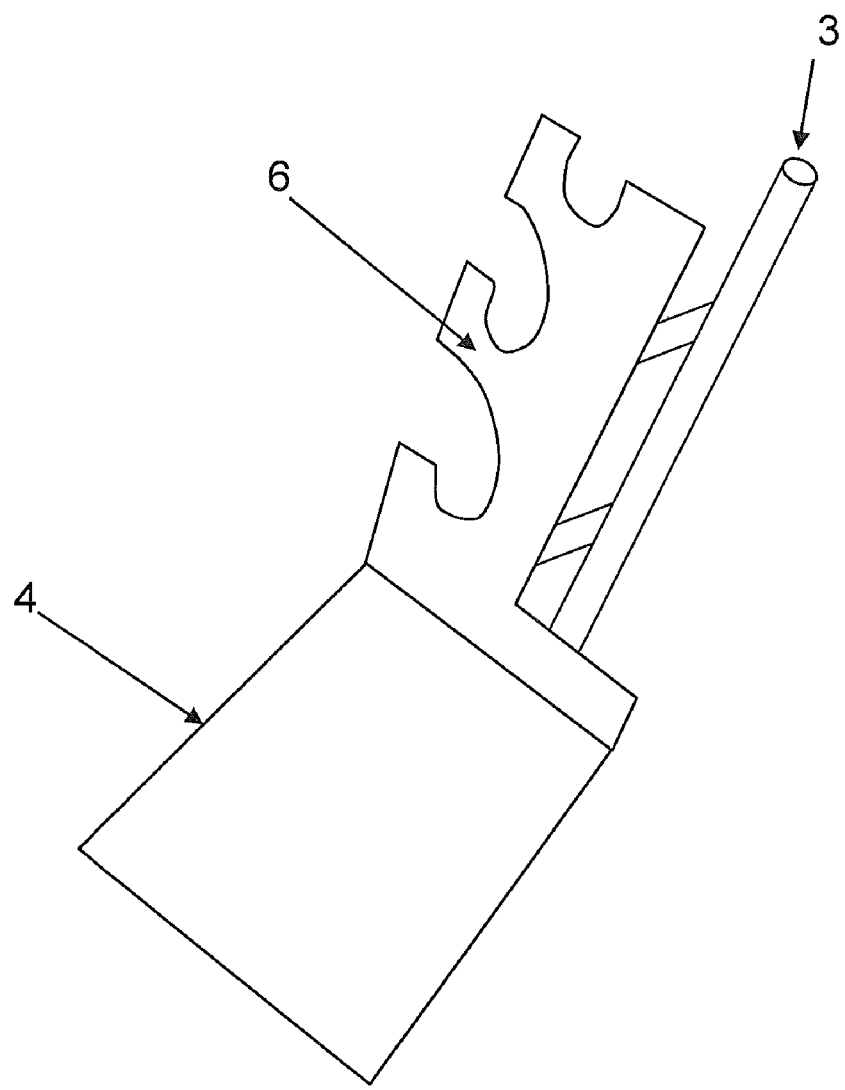
FIG. 3 is a depiction of another preferred embodiment of the invention wherein support for additional equipment is found on one side of the pole to which a transducer holder is attached.

In a further embodiment, as set forth in FIG. 3, the supports (6) may be only on one side of the pole (3). This allows for additional types of holders to be clamped to the dowel or pole without interference from the "breathing device" portion of the device.

In yet another embodiment, the bracket can have a clamp in place of the base (4). The clamp can be attached directly to the bed.

This device can additionally be used as a leveling device for any object that would need to maintain a constant relationship between two objects. In this case a constant relationship between the device and either the patient's atrium or middle ear is desirable. There might be a need to have a similar device to extend over a patient or above a patient and maintain a certain relationship between itself and the patient or between itself and a surgical tool or between two or more surgical tools. A larger device could be placed under a patients' mattress while it is being used in the intensive care unit. It would serve the same purpose presented. It could also be modified and made of stronger material to additionally mount infusion pumps for patient transport and thereby eliminate or modify an intravenous pole. This would allow for attachment to the patient care bed. It could be used in intensive care settings and modified in size for those locations where these invasive monitors are used to monitor these "pressures". It could also be modified to help support a Transesophageal Echo (TEE) probe which is routinely used during Cardiac surgery in the operating room.

An additional advantage of the device of the invention is that it can be readily transferred from one bed to another as the patient is moved. This will help maintain the correct height of the instruments and also prevent the necessity of detaching equipment from one bracket and reassembling it on another.

Although the invention is illustrated and described herein with reference to specific embodiments, the invention is not intended to be limited to the details shown. Rather, various modifications may be made in the details with the scope and range of equivalents of the claims and without departing from the invention.

The invention claimed is:

1. A support for holding medical equipment which comprises
   a. a pole extending vertically upwardly from a base;
   b. a bracket rigidly attached to the pole;
   c. the base which is adapted to hold the bracket to a bed at a constant height;
   wherein the pole extends above and below the bracket, the bracket contains slots in which medical equipment can be positioned, and the position of the bracket on the pole can be adjusted.

2. The support of claim 1 wherein the bracket extends horizontally on both sides of the pole.

3. The support of claim 1 wherein the bracket extends horizontally on one side of the pole.

* * * * *